United States Patent [19]
Yamada et al.

[11] Patent Number: 4,922,039
[45] Date of Patent: May 1, 1990

[54] PROCESS FOR SEPARATING DICHLOROCUMENE ISOMER

[75] Inventors: Bunshi Yamada; Michio Kimura; Yoshio Noguchi, all of Aichi, Japan

[73] Assignee: Toray Industries, Tokyo, Japan

[21] Appl. No.: 290,023

[22] Filed: Dec. 27, 1988

[30] Foreign Application Priority Data

Dec. 28, 1987 [JP] Japan ................... 62-335015

[51] Int. Cl.$^5$ ............................................ C07C 17/38
[52] U.S. Cl. ...................................................... 570/211
[58] Field of Search ......................................... 570/211

[56] References Cited

U.S. PATENT DOCUMENTS

| 4,254,062 | 3/1981 | Wambach et al. | 570/211 |
| 4,329,524 | 5/1982 | Dewald | 570/ |
| 4,774,371 | 9/1988 | Miwa et al. | 570/211 |

FOREIGN PATENT DOCUMENTS 2538379  6/1984  France ................................. 570/

OTHER PUBLICATIONS

Chen et al. *Chemical Engineering Progress* Feb. 1988, pp. 32–40.

Primary Examiner—Werren B. Lone
Attorney, Agent, or Firm—Austin R. Miller

[57] ABSTRACT

A specific isomer of dichlorocumene is separated from a mixture containing dichlorocumene isomers by adsorptive separation, wherein the zeolite having at least 2 of silica/alumina molar ratio and 0.6 to 1.0 nm of pore size is used as the adsorbent and halogenated benzene or halogenated alkyl benzene is used as desorbent.

5 Claims, 1 Drawing Sheet

PROCESS FOR SEPARATING DICHLOROCUMENE ISOMER

BACKGROUND OF THE INVENTION (1) Field of the Invention

This invention relates a process for separating a specific isomer of dichlorocumene from a mixture containing dichlorocumene isomers.

(2) Description of the Prior Art

Dichlorocumene, in particular, 3,5-dichlorocumene (hereinafter referred to as "3,5-DCC") is important an intermediate substance for agricultural chemicals, medicines and dyes.

Dichlorocumene is obtained by reacting dichlorobenzene with propylene or isopropyl halide in the presence of a catalyst. In particular, 3,5-DCC is obtained by isomerization of 2,4-dichlorocumene (hereinafter referred to as "2,4-DCC") in the presence of the catalyst. 2,4-DCC is obtained by alkylation of m-dichlorobenzene (hereinafter referred to as "m-DCB"). The resulting isomer mixture of dichlorocumene contains mainly 2,4-DCC and 3,5-DCC at thermal equilibrium and further contains unreacted material from m-DCB, a by-product 2,5-dichlorocumene (hereinafter referred to as "2,5-DCC"), and a by product dichlorodiisopropylbenzene (hereinafter referred to as "DCDIPB"), and also contains the catalyst. From the reaction mixture containing dichlorocumene isomers, the catalyst is removed by filtration, and unreacted m-DCB and DCDIPB which high boiling points are removed by distillation. However, considerable difficulties are encountered in separation of a dichlorocumene isomer from the mixture of dichlorocumene isomers by distillation because their boiling points are very close to one another. Therefore, in the past, the mixture of dichlorocumene isomers was alkylated, whereby 2,4-DCC was selectively converted to DCDIPB, and thereafter the 3,5-DCC was separated by distillation (U.S. Pat. No. 4,104,315).

However, since the thus obtained 3,5-DCC still contains a small amount of unreacted 2,4-DCC and by-product 2,5-DCC, the 3,5-DCC is selectively brominated and can be separated and purified by distillation (U.S. Pat. No. 4,087,473).

Recovered unreacted m-DCB and by-product DCDIPB are fed to the prior alkylation process, whereby m-DCB and DCDIPB are converted to 2,4-DCC by transalkylation and reused (U.S. Pat. No. 4,329,524).

However, the prior separation purification process which repeats reactions and distillation such as alkylation (first)—isomerization—removal of catalyst—distillation—alkylation(second)—distillation—bromination—distillation is disadvantageous for economical and industrial use.

Moreover, the repetition of the reaction give rise to the increase of undesirable by-product. In the prior art, the problem is retained as both economical disadvantage and low quality of the product.

SUMMARY OF THE INVENTION

One object of the present invention is to provide a process for separating selectively a specific dichlorocumene isomer from a mixture containing dichlorocumene isomers, at a high efficiency.

Another object of the present invention is to provide a process for separating dichlorocumene isomer using an adsorbent having high capacity for adsorbing a specific dichlorocumene isomer.

Another object of the present invention is to provide a process for separating dichlorocumene isomer using an desorbent having desirable ability of expelling the isomer adsorbed in the adsorbent.

A further object of the present invention is to provide a process for separating 3,5-DCC from a mixture containing dichlorocumene isomers at a high efficiency.

Other and further objects, features, and advantages of the invention will appear more fully from the following description.

These objects are attained by a process for separating dichlorocumene isomer from a mixture containing dichlorocumene isomers, comprising contacting the isomer mixture with a zeolite adsorbent having a silica/alumina molar ratio of at least and a pore size of 0.6 to 1.0 nm.

DETAILED DESCRIPTION OF PREFERRED EMBODIMENTS

Figure 1:
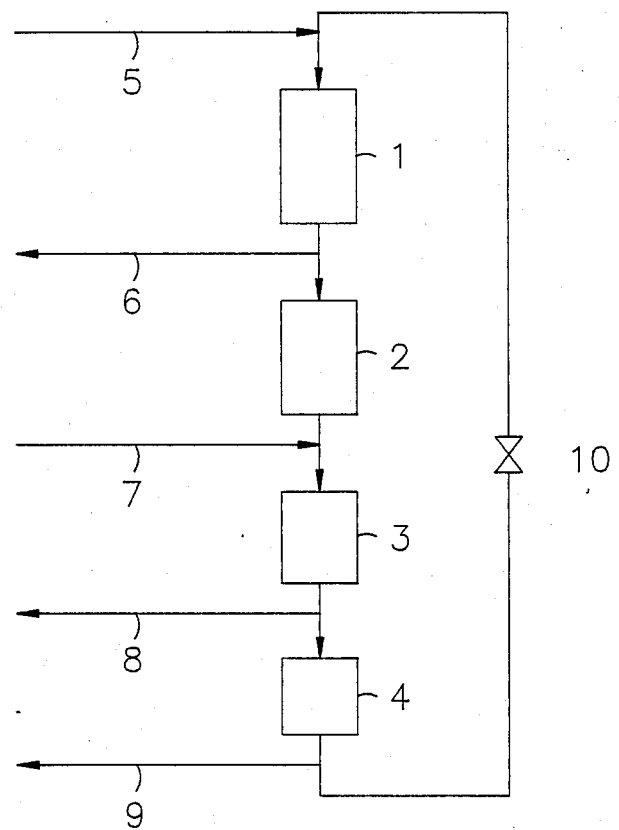
FIG. 1 is a flow sheet illustrating continuous adsorptive separation of dichlorocumene isomer using a simulated moving bed.

The present invention will be explained in detail.

The mixture containing dichlorocumene isomers in the present invention, is a mixture of dichlorocumenes which usually contains mainly 2,4-DCC, 2,5-DCC and 3,5-DCC and further contains by-products of DCDIPB.

The zeolite that is used as adsorbent in the present invention is a zeolite having a silica/alumina molar ratio of at least 2 of and a pore size of 0.6 to 1.0 nm.

Zeolite is a crystal consisting of a three dimensional network structure, wherein a regular tetrahedron of $SiO_4$ and a regular tetrahedron of $AlO_4$ are combined by sharing an oxygen atom. According to the combination mode, zeolite has various kinds of shapes of voids and pore paths. The entrance of such a void is called a pore and the pore has a uniformly significant diameter (hereinafter referred to as "pore size"). This pore size can be variable a little according to the crystal structure of zeolite and kinds of cations corresponding to the minus charge of $AlO_4$. Zeolites used in the present invention need to have pore sizes of 0.6 to 1.0 nm. If the pore size is less than 0.6 nm or more than 1.0 nm, dichlorocumene isomer cannot be separated by adsorption separation.

Moreover, the zeolite used in the present invention needs to have a silica/alumina ratio of at least 2, preferably 2 to 30. If the silica/alumina molar ratio is less than 2, dichlorocumene isomers cannot be separated by adsorption separation.

Whenever any zeolite has these characteristics, namely, having a silica/alumina molar ratio of at least 2 and a pore size of 0.6 to 1.0 nm, it can be included in the range of the present invention.

As preferable examples of a zeolite having a silica/alumina molar ratio of at least 2 and a pore size of 0.6 to 1.0 nm, used in the present invention, for example, are faujasite type zeolite, L type zeolite, beta type zeolite, mordenite type zeolite, pentasil type zeolite, omega type zeolite, and offretite type zeolite. More preferably, faujasite type zeolite, L type zeolite, beta type zeolite are used in the present invention.

The faujasite type zeolite used in the present invention is a crystalline aluminosilicate represented by the following formula:

$$(0.9\pm0.2)M_{2/n}O:Al_2O_3:xSiO_2:yH_2O$$

wherein M stands for a cation selected from proton, ammonium ion, univalent metal cation, divalent metal cation, and trivalent cation; n indicates the valency of the cation M; and the value of y differs according to the degree of hydration.

The faujasite type zeolite represented by the above formula is classified into type X in which x in the above formula is in the range of 2.5±0.5 and type Y in which x in the above formula is from 3 to 6. That is, type X zeolites have 2.5±0.5 silica/alumina molar ratios and type Y zeolites have 3 to 6 silica/alumina molar ratios. Both type X zeolite and type Y zeolite typically have about 0.74 nm pore size, but have 0.6 to 0.9 nm pore size by changing the cation of zeolite.

The L type Zeolite used in the present invention is a crystalline aluminosilicate represented by the following formula:

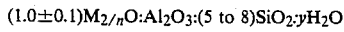
$$(1.0\pm0.1)M_{2/n}O:Al_2O_3:(5\text{ to }8)SiO_2:yH_2O$$

wherein M stands for a cation selected from proton, ammonium ion, univalent metal cation, divalent metal cation, and trivalent cation; n indicates the valency of the cation M; and the value of Y is an optional number of 0 to 7. That is, L type zeolites have 5 to 8 silica/alumina molar ratios and typically have about 0.71 nm pore size, but have 0.6 to 0.9 nm pore size by changing the cation of zeolite.

The beta type Zeolite used in the present invention is a crystalline aluminosilicate represented by the following formula:

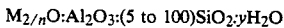
$$M_{2/n}O:Al_2O_3:(5\text{ to }100)SiO_2:yH_2O$$

wherein M stands for a cation selected from proton, ammonium ion, univalent metal cation, divalent metal cation, and trivalent cation; n indicates the valency of the cation M; and the value of y differs according to the degree of hydration. That is, beta type zeolites may have 5 to 100 silica/alumina molar ratios and have 0.6 to 0.9 nm pore sizes by changing cation of zeolite.

It is also preferred that the cation M be at least one member selected from metals of the groups IA, IB and IIA of the Periodic Table, proton and ammonium ion, and it is especially preferred that the cation be at least one member selected from lithium, sodium, potassium, magnesium, calcium, strontium, barium, copper, silver, gold, proton, and ammonium.

These cations can be introduced into the adsorbent by ion exchange. Any of known ion exchange processes can optionally be adopted. Ordinarily, the ion exchange is effected with an aqueous solution containing a water-soluble salt of a required cation or an aqueous solution containing an ammonium salt. Proton is introduced as the cation into the adsorbent by calcinating the zeolite ion exchanged by ammonium salt.

Zeolites used in the present invention are obtained by optional methods, for example, by methods described in Japanese Unexamined Patent Publication No. 28126/1978, Japanese Examined Patent Publication No. 3675/1961, or U.S. Pat. No. 3,308,069.

The adsorptive separation of dichlorocumene isomer according to the present invention may be accomplished by ordinary methods, for example, chromatographic separation or continuous adsorptive methods using a simulated moving bed.

In the continuous adsorptive separation technique according to the present invention, a simulated moving bed having a plurality of adsorption chambers filled with an adsorbent is used. This adsorptive separation technique comprises as the basic operations, an adsorption operation, a concentration operation, a desorption operation and a desorbent recovery operation, which are continuously repeated. These basic operations are as follows.

(1) Adsorption Operation

A starting mixture containing dichlorocumene isomers is brought into contact with a bed of an adsorbent and a highly adsorbable component is selectively adsorbed. The remaining weakly adsorbable component is withdrawn from the adsorbent bed together with a desorbent in the form of a raffinate flow.

(2) Concentration Operation

The adsorbent having the strongly adsorbable component selectively adsorbed therein is brought into contact with a part of an extract described hereinafter to expel the weakly adsorbable component left on the adsorbent and increase the purity of the strongly adsorbable component.

(3) Desorption Operation

The adsorbent bed containing the strongly adsorbable component having increased purity is brought into contact with the desorbent and the highly adsorbable component having the increased purity is withdrawn from the adsorbent bed together with the desorbent in the form of an extract flow.

(4) Recovery Operation

The adsorbent bed containing the desorbent is brought into contact with a part of the raffinate flow and the desorbent is withdrawn from the adsorbent bed.

Typical examples of the simulated moving bed operation will be described hereinafter in the working examples with reference to the accompanying drawings.

The simulated moving bed used will now be described with reference to FIG. 1. Four adsorption chambers 1 through 4 are connected in series, and reference numerals 5, 6, 7, 8 and 9 represent a desorbent feed line, an extract withdrawal line, a feed supply line, a raffinate withdrawal line and a desorbent recovery line, respectively. The desorption operation is carried out in the adsorption chamber 1, the concentration operation is carried out in the adsorption chamber 2, the adsorption operation is carried out in the adsorption chamber 3, and the recovery operation is carried out in the adsorption chamber 4. The liquid flows downward as viewed in the drawings. The line between the adsorption chamber 1 to 4 is closed by a valve 10. The extract and raffinate flows are separated into dichlorocumene isomer components and desorbent component by rectifier columns.

At predetermined time intervals (hereinafter referred to as "changeover time"), the lines 5 thorough 9 and valve 10 are transferred counter clockwise by one adsorption chamber. If it is assumed that the above-mentioned lines and valve are kept stationary in FIG. 1, it may be considered that the adsorption chambers 1 to 4 are apparently transferred clockwise by one extract flow was withdrawn from line 6. The above-mentioned dichlorocumene isomer mixture was supplied from the line 7 and a raffinate flow was withdrawn from the line 8. The remaining liquid was withdrawn from the line 9.

The desorbent used in the present adsorptive separation method is one or more compound selected from the group consisting of halogenated alkyl benzene and halogenated benzene. For example, chlorotoluene, dichlorobenzene, dichlorotoluene can be preferably used. These compounds may use soley or the mixtures containing at least two compounds as a desorbent. One isomer of these compounds may be used or a mixture of optional isomers may be used as a desorbent.

The adsorptive separation is carried out at a temperature of from room temperature to 350° C., preferably from 50° to 250° C., under a pressure of from atmospheric pressure to 50 Kg/cm²G, preferably from atmospheric pressure to 40 Kg/cm²G. In the present invention, the adsorptive separation may be carried out either in the vapor phase or in the liquid phase. However, in order to prevent occurrence of an undesirable side reaction in the starting mixture or desorbent, it is preferred that the operation be carried out at a low temperature in the liquid phase.

The process of the present invention will now be described in detail with reference to the following Examples.

In the examples, the adsorbing characteristic of the adsorbent is expressed by the following adsorptive selectivity $\alpha_{A/B}$:

$$\alpha_{A/B} = \frac{[(\text{weight percent of component } A)/(\text{weight percent of component } B)]_S}{[(\text{weight percent of component } A)/(\text{weight percent of component } B)]_L}$$

In the above formula, A and B designate dichlorocumene isomers respectively, S designates the adsorbed phase, and L designates the liquid phase equilibrated with the adsorbed phase.

If the value $\alpha_{A/B}$ is larger than unity, the component A is selectively adsorbed and if the value $\alpha_{A/B}$ is smaller than unity, the component B is selectively adsorbed. If the value $\alpha_{A/B}$ is much larger than unity (or is smaller than unity and closer to zero) in the adsorbent, the adsorptive separation of components A and B becomes easier.

In the examples, the desorbing characteristic of the desorbent is expressed by the following adsorptive selectivity $\alpha_{DES/DCC}$:

$$\alpha_{DES/DCC} = \frac{[(\text{weight percent of component } DES)/(\text{weight percent of component } DCC)]_S}{[(\text{weight percent of component } DES)/(\text{weight percent of component } DCC)]_L}$$

In the above formula, DES designates desorbent, and DCC designates dichlorocumene isomer being adsorbed most strongly by the adsorbent, S designates the adsorbed phase, and L designates the liquid phase equilibrated with the adsorbed phase.

The value $\alpha_{DES/DCC}$, most preferably, is close to unity. If the value $\alpha_{DES/DCC}$ is larger than unity, the desorption is strongly carried and the next adsorption becomes difficult. If the value $\alpha_{DES/DCC}$ is smaller than unity and closer to zero, adsorbed dichlorocumene isomer can not be fully desorbed.

EXAMPLE 1

A granular zeolite of the Na-Y type having 5.5 silica/alumina molar ratio and about 0.74 nm pore size was subjected to ion-exchange treatment with an aqueous solution of cation-equivalent potassium nitrate with at a solid/liquid ratio of 5 ml/g at 90° C. for 2 hours. This treatment was repeated ten times to replace more than 98 mol % of the sodium ion with the potassium ion and thereby prepare an adsorbent of K-Y zeolite. After ion-exchange, the resulting K-Y zeolite was washed with pure water at a solid/liquid ratio of 5 ml/g at 90° C. at ten times, then dried at 120° C. overnight.

Thus obtained K-Y zeolite was calcined at 500° C. for 2 hours, just before the adsorptive selectivity of this adsorbent of the K-Y zeolite for adsorption of dichlorocumene isomers.

In order to determine the adsorptive selectivity of this adsorbent of K-Y zeolite for adsorption of dichlorocumene isomers containing DCDIPB, about 2 g of the K-Y zeolite and 2.5 ml of the mixture containing dichlorocumene isomers [Mixture A] were charged into an autoclave having an inner capacity of 5 ml and heated at 150° C. for 0.5 hour while stirring now and then. The mixture containing dichlorocumene isomers [Mixture A] charged comprised as follows;

| [Mixture A] | |
|---|---|
| 2,4-DCC | 36 (weight parts) |
| 2,5-DCC | 1 |
| 3,5-DCC | 56 |
| DCDIPB | 7 | n-Nonane was added as the internal standard substance for gas-chromatographical analysis, and it was substantially inactive relatively to the adsorption under the experimental conditions. The composition of the liquid-phase mixture after contact with the adsorbent was analyzed by gas chromatography, and the adsorptive selectivities for the dichlorocumene isomers were calculated according to the above-mentioned formula. The obtained results are shown in Table 1.

EXAMPLE 2 TO 6

Instead of the zeolite of the Na-Y type, Na-beta zeolite having 20.0 of silica/alumina molar ratio was subjected to the ion-exchange treatment in the same manner as described in Example 1 to give K-beta zeolite.

Na-Y zeolite having 4.8 silica/alumina molar ratio and about 0.74 nm the pore size was subjected to the ion-exchange treatment with an aqueous solution of barium nitrate in the same manner as described in Example 1 to give Ba-Y zeolite.

Na-Y zeolite having 4.8 silica/alumina molar ratio and about 0.74 nm the pore size was subjected to the ion-exchange treatment with each an aqueous solution containing 0.15 cation-equivalent ammonium nitrate and 0.85 cation-equivalent of potassium nitrate and an aqueous solution containing 0.3 cation-equivalent ammonium nitrate and 0.7 cation-equivalent of potassium nitrate in the same manner as described in Example 1 to give 0.15H-K-Y zeolite and 0.3H-K-Y zeolite, respectively. The resulting 0.15H-K-Y zeolite and 0.3H-K-Y zeolite were calcined, whereby ammonium was protonated.

K-L zeolite having 6.1 silica/alumina molar ratio and about 0.71 nm pore size, the resulting K-beta zeolite, the resulting 0.15H-K-Y zeolite and the resulting 0.3H-K-Y zeolite were tested in the same manner as described in Example 1, and the adsorptive selectivities for the dichlorocumene isomers were determined. The obtained results are shown in Table 1.

TABLE 1

| Example No. | Zeolite Adsorbent | SiO$_2$/Al$_2$O$_3$ molar ratio | $\alpha\frac{3,5\text{-DCC}}{2,5\text{-DCC}}$ | $\alpha\frac{3,5\text{-DCC}}{2,4\text{-DCC}}$ | $\alpha\frac{3,5\text{-DCC}}{\text{DCDIPB}}$ |
|---|---|---|---|---|---|
| 1 | K—Y | 5.5 | 1.42 | 1.78 | 4.18 |
| 2 | K—L | 6.1 | 0.50 | 0.51 | 0.70 |
| 3 | K—beta | 20.0 | 0.34 | 0.38 | 0.68 |
| 4 | Ba—Y | 4.8 | 1.68 | 1.50 | 4.35 |
| 5 | 0.15H—K—Y | 4.8 | 1.62 | 1.82 | 5.40 |
| 6 | 0.3H—K—Y | 4.8 | 1.77 | 1.71 | 5.35 |

EXAMPLE 7 TO 13

Each Na-X zeolite having 2.5 of silica/alumina molar ratio and about 0.74 nm pore size and Na-Y zeolite having 4.8 silica/alumina molar ratio and about 0.74 nm pore size was subjected to the ion-exchange treatment in the same manner as described in Example 1 to give the various zeolite adsorbents shown in Table 2.

The resulting zeolite adsorbents shown in Table 1 were tested using the following mixture containing dichlorocumene isomers [Mixture B] in the same manner as described in Example 1, and the adsorptive selectivities for the dichlorocumene isomers were determined. The obtained results are shown in Table 2.

[Mixture B]

| 2,4-DCC | 40 (weight parts) |
|---|---|
| 3,5-DCC | 60 |

TABLE 2

| Example No. | Zeolite Adsorbent | SiO$_2$/Al$_2$O$_3$ molar ratio | $\alpha\frac{3,5\text{-DCC}}{2,4\text{-DCC}}$ |
|---|---|---|---|
| 7 | K—X | 2.5 | 1.18 |
| 8 | Na—X | 2.5 | 1.25 |
| 9 | 0.3-Ag—Na—Y | 4.8 | 1.23 |
| 10 | Na—Y | 4.8 | 1.74 |
| 11 | Mg—Y | 4.8 | 1.44 |
| 12 | Ca—X | 2.5 | 0.81 |
| 13 | Sr—X | 2.5 | 1.50 |

COMPARATIVE EXAMPLE 1

Na-A type zeolite having 2.0 silica/alumina molar ratio and about 0.42 nm pore size was tested in the same manner as described in Example 1. However neither dichlorocumene isomer nor the DCDIPB was adsorbed. It was impossible to separate any dichlorocumene isomer from the mixture containing dichlorocumene isomers.

EXAMPLE 14 TO 23

The 0.15H-K-Y zeolite obtained by Example 5 was tested using the following mixture containing dichlorocumene isomers and each desorbent shown in Table 3 [Mixture C] in the same manner as described in Example 1, and the adsorptive selectivities for the dichlorocumene isomers and the adsorptive selectivities for the dichlorocumene isomer and the desorbent were determined. The obtained results are shown in Table 3.

[Mixture C]

| Desorbent shown in Table 3 | 50 (weight parts) |
|---|---|
| 2,4-DCC | 15 |
| 2,5-DCC | 15 |
| 3,5-DCC | 20 |

TABLE 3

| Example No. | Desorbent (DES) | $\frac{\text{DES}}{3,5\text{-DCC}}$ | $\frac{3,5\text{-DCC}}{2,4\text{-DCC}}$ | $\frac{3,5\text{-DCC}}{2,5\text{-DCC}}$ |
|---|---|---|---|---|
| 14 | o-chlorotoluene | 2.25 | 2.68 | 2.40 |
| 15 | m-chlorotoluene | 2.30 | 1.72 | 1.61 |
| 16 | m-dichlorobenzene | 1.80 | 1.70 | 1.74 |
| 17 | 2,4-dichlorotoluene | 1.85 | 1.70 | 1.50 |
| 18 | 2,5-dichlorotoluene | 0.74 | 1.61 | 1.54 |
| 19 | 2,6-dichlorotoluene | 1.33 | 1.61 | 1.33 |
| 20 | 3,4-dichlorotoluene | 2.38 | 2.02 | 1.51 |
| 21 | 3,5-dichlorotoluene | 0.70 | 2.02 | 1.50 |
| 22 | mixture of dichlorotoluene[a] | 1.09 | 1.78 | 1.75 |
| 23 | mixture of dichlorotoluene[b] | 1.70 | 2.02 | 1.72 |

[a] is the mixture of 34% of 2,4-dichlorotoluene, 63% of 2,5-dichlorotoluene, 2% of 2,6-dichlorotoluene, and 1% of 2,3-dichlorotoluene.
[b] is the mixture of 35.6% of 2,4-dichlorotoluene, 38.5% of 2,5-dichlorotoluene, 7.5% of 2,6-dichlorotoluene, 7.4% of 3,4-dichlorotoluene, 3.0% of 3,5-dichlorotoluene and 8.0% of 2,3-dichlorotoluene.

COMPARATIVE EXAMPLE 2 to 14

The 0.15H-K-Y zeolite obtained by Example 5 was tested using the following mixture containing dichlorocumene isomers and each desorbent shown in Table 4 [Mixture D] in the same manner as described in Example 1, and the adsorptive selectivities for the dichlorocumene isomers and the adsorptive selectivities for the dichlorocumene isomer and the desorbent were determined. The obtained results are shown in Table 4.

[Mixture C]

| Desorbent shown in Table 4 | 50 (weight parts) |
|---|---|
| 2,4-DCC | 15 |
| 2,5-DCC | 15 |
| 3,5-DCC | 20 |

TABLE 4

| Comparative Example No. | Desorbent (DES) | $\alpha\frac{\text{DES}}{3,5\text{-DCC}}$ | $\alpha\frac{3,5\text{-DCC}}{2,4\text{-DCC}}$ | $\alpha\frac{3,5\text{-DCC}}{2,5\text{-DCC}}$ |
|---|---|---|---|---|
| 2 | benzene | 4.15 | 1.93 | 2.34 |
| 3 | toluene | 4.72 | 1.04 | 1.08 |
| 4 | ethylbenzene | 57 | 0.34 | — |

TABLE 4-continued

| Comparative Example No. | Desorbent (DES) | $\alpha \dfrac{\text{DES}}{\text{3,5-DCC}}$ | $\alpha \dfrac{\text{3,5-DCC}}{\text{2,4-DCC}}$ | $\alpha \dfrac{\text{3,5-DCC}}{\text{2,5-DCC}}$ |
|---|---|---|---|---|
| 5 | n-propylbenzene | 4.72 | 1.27 | 1.41 |
| 6 | cumene | 6.36 | 1.02 | 0.87 |
| 7 | pseudocumene | 4.86 | 1.64 | 1.31 |
| 8 | mesitylene | 4.04 | 1.06 | 2.70 |
| 9 | p-cymene | 20 | 1.43 | 1.36 |
| 10 | m-diethylbenzene | 6.77 | 1.42 | 1.66 |
| 11 | o,m,p-diethylbenzene mixture | 5.85 | 1.33 | 2.36 |
| 12 | benzaldehyde | 470 | 0.15 | 0.29 |
| 13 | diethylketone | 500 | — | 0.18 |
| 14 | cyclohexanone | 1600 | 0.49 | 1.18 |

EXAMPLE 24

3,5-DCC isomer was separated from the mixture containing dichlorocumene isomer and DCDIPB comprising the following composition, using the simulated moving bed as shown in FIG. 1.

| | |
|---|---|
| 3,5-DCC | 63.3% |
| 2,4-DCC | 35.6% |
| 2,5-DCC | 0.7% |
| DCDIPB | 0.4% |

K-Y zeolite obtained in Example 1 was charged into four adsorption chamber 1, 2, 3, and 4, all of them having an inner capacity of about 40 ml respectively. The above-mentioned mixture containing dichlorocumene isomers was supplied at a rate of 12.6 ml/hr form the line 7, and the dichlorotoluene mixture having the following composition as desorbent was supplied at a rate of 422 ml/hr from the line 5.

| | |
|---|---|
| 2,4-dichlorotoluene | 34% |
| 2,5-dichlorotoluene | 63% |
| 2,6-dichlorotoluene | 2% |
| 2,3-dichlorotoluene | 1% |

The extract flow was withdrawn at a rate of 61.7 ml/hr from the line 6, and the raffinate flow was withdrawn at a rate of 66.9 ml/hr from the line 8. The remaining liquid was withdrawn from the line 9. The line between adsorption chamber 1 and 4 was closed by a valve 10. At every changeover time of 150 seconds, the adsorption chamber 1 was transferred to the adsorption chamber 4, the adsorption chamber 4 was transferred to the adsorption chamber 3, the adsorption chamber 3 was transferred to the adsorption chamber 2, and the adsorption chamber 2 was transferred to the adsorption chamber 1, simultaneously.

The adsorption temperature was 170° C. and the adsorption pressure was 20 kg/cm$^2$.

The purity of 3,5-DCC in the DCC component in the extract flow was 99.8% and the recovery ratio of 3,5-DCC was 91.7%.

What we claim is:

1. A process for separate 3,5-dichlorocumene isomer from a mixture consisting substantially of dichlorocumene isomers by absorptive separation, which comprises contacting the isomer mixture with a zeolite adsorbent having a silica/alumina molar ratio of at least 2 and a pore size of 0.6 to 1.0 nm, and eluting the adsorbed isomer by contacting the zeolite adsorbent with a desorbent selected from the group consisting of halogenated benzene and halogenated alkyl benzene.

2. A process according to claim 1, wherein said zeolite is selected from the group consisting of type X, type Y, type L and type beta zeolite.

3. A process according to claim 1, wherein said zeolite is substituted by a cation selected from the group consisting of proton, ammonium, and metal cation of the groups IA, IB and IIA of the Periodic Table.

4. A process according to claim 3, wherein said cation is selected from the group consisting of lithium, sodium, potassium, magnesium, calcium, strontium, barium, copper, silver, gold, proton, and ammonium.

5. A process according to claim 1, wherein said desorbent is selected from the group consisting of chlorotoluene, dichlorobenzene, dichlorotoluene.

* * * * *

UNITED STATES PATENT AND TRADEMARK OFFICE
CERTIFICATE OF CORRECTION

PATENT NO. : 4,922,039
DATED : May 1, 1990
INVENTOR(S) : Bunshi Yamada et al It is certified that error appears in the above-identified patent and that said Letters Patent is hereby corrected as shown below:

Column 1, line 57, delete "give" and insert therefor --gives--.

Column 2, line 17, after "least" insert --2--.

Column 5, line 8, delete "the" and insert therefor --as--.

Column 6, line 51, delete "the", both occurrences.

Column 7, line 18, delete "of".

Column 10, line 27, delete "separate" and insert therefor --separating--.

Column 5, line 8, delete "use" insert --be used--.

Signed and Sealed this

Eighteenth Day of August, 1992

Attest:

DOUGLAS B. COMER

*Attesting Officer*  *Acting Commissioner of Patents and Trademarks*